US00PP19362P2

(12) United States Plant Patent
Kordes

(10) Patent No.: US PP19,362 P2
(45) Date of Patent: Oct. 21, 2008

(54) SHRUB ROSE PLANT NAMED 'KORFLOCI08'

(50) Latin Name: *Rosa hybrida*
Varietal Denomination: KORfloci08

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/008,683

(22) Filed: Jan. 11, 2008

(51) Int. Cl.
*A01H 5/00* (2006.01)

(52) U.S. Cl. ..... Plt./105
(58) Field of Classification Search ..... Plt./105
See application file for complete search history.

*Primary Examiner*—Annette H Para

(57) ABSTRACT

A new and distinct variety of rose with long lasting, novel orange-red colored flowers, and attractive foliage with good disease resistance. It exhibits compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci08'.

BACKGROUND OF THE INVENTION

The new variety of rose plant of the present invention originated from a controlled crossing in a breeding program of two distinct parents during the summer of 2000. The crossing was between 'NOAcas' and 'KORparesni'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci08'.

SUMMARY OF THE INVENTION

The new rose plant may be distinguished from its seed parent, 'NOAcas' by the following combination of characteristics:

1. The flowers of 'KORfloci08' are orange red, while the flowers of the seed parent are red,
2. The growth habit of 'KORfloci08' is compact, while the growth habit of the seed parent is spreading, and
3. The flower size of 'KORfloci08' is medium, while the flower size of the seed parent is small.

The new rose plant may be distinguished from its pollen parent, 'KORparesni' by the following combination of characteristics:

1. The flowers of 'KORfloci08' are orange red, while the flowers of the pollen parent are pink,
2. The growth habit of 'KORfloci08' is compact, while the growth habit the pollen parent is upright, and
3. 'KORfloci08' exhibits better disease resistance than the pollen parent.

The objective of the hybridization was to create a new and distinct rose plant with unique qualities, such as:

1. Compact and uniform growth and flowering;
2. Abundant attractive, recurrent flowers;
3. Attractive and abundant foliage; and
4. Resistance to diseases encountered in landscapes and gardens.

This combination of qualities is not present in prior rose cultivars. These objectives have been substantially achieved and in that distinguish 'KORfloci08' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci08' was selected in May, 2001 from the seedling beds to be asexually propagated for further evaluation. The first asexual propagation of 'KORfloci08' was done by budding to seedling understocks in July, 2001 at the inventor's nursery in Offenseth-Sparrieshoop, Germany.

This initial and other subsequent propagations conducted in controlled environments demonstrate that 'KORfloci08' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORfloci08'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORfloci08', as observed growing in September 2007 in a nursery in Jackson County, Oregon on plants of four years of age. Color references are made using The Royal Horticultural Society (London, England) Colour Chart, 2001 except where common terms of color are used.

For a comparison, several physical characteristics of the rose variety 'KORtemma', a rose variety from the same inventor described and illustrated in U.S. Plant Pat. No. 9,115 and issued on Apr. 25, 1995 are compared to 'KORfloci08' in Chart 1.

CHART 1

| Characteristic | 'KORfloci08' | 'KORtemma' |
|---|---|---|
| Growth habit | Compact | Spreading |
| Petal count | 40-45 | 20 |
| Bud color as sepals first unfold | Orange-Red Group 34A | Red Group 46A |

Parents:

*Seed parent.*—'NOAcas'.

*Pollen parent.*—'KORparesni'.

Classification:

*Botanical classification.*—*Rosa hybrida*, 'KORfloci08'.

*Commercial classification.*—Shrub.

FLOWER AND FLOWER BUD

Blooming habit: Recurrent.

Flower bud:

*Size.*—Upon opening, 27–29 mm in length from base of receptacle to end of bud and 15–16 mm diameter at its widest point.

*Bud form.*—Medium. Pointed-ovoid to globular.

*Bud color.*—As sepals first unfold, bud color is Orange-Red Group 34A. When ¼ open, the upper surface of petals is Red Group 44B, and the lower surface is Red Group 45C.

*Sepals.*—Size: Average 18–22 mm long×6–7 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner surface: Covered in fine white hairs. Outer surface: Smooth. Stipitate glands are present. Color: Upper surface Yellow-Green Group 144B. Lower surface Yellow-Green Group 144A.

*Receptacle.*—Surface: Smooth. Color: Yellow-Green Group 144A. Shape: Funnel. Size: 7–9 mm (h)×5–7 mm (w).

*Peduncle.*—Surface: Few stipitate glands. Length: 30 mm average length. Diameter: 1–1.5 mm average diameter. Color: Yellow-Green Group 145A. Strength: Somewhat strong. Borne: Multiple flower buds per stem, generally 3 to 5.

Flower bloom:

*Fragrance.*—Very light spicy fragrance.

*Duration.*—On the plant 6 to 8 days. Senesced petals drop away cleanly.

*Size.*—Medium sized blooms. When open, the average flower diameter is 60–70 mm and the average flower height is 30 mm.

*Form.*—Shape of flower when viewed from the side: Upon opening, upper part: Flat. Upon opening, lower part: Flattened convex. Open flower, upper part: Flattened convex to convex. Open flower, lower part: Concave.

Color:

*Upon opening, petals.*—Outermost petals: Outer Side: Red Group 50B. Inner Side: Orange-Red Group N30A. Innermost petals: Outer Side: Red Group 50A. Inner Side: Orange-Red Group N30A.

*Upon opening, basal petal spots.*—Basal petal spot, outermost petals: Outer Side: Yellow-Green Group 150D. Inner Side: Yellow-Green Group 149D. Basal petal spot, innermost petals: Outer Side: Yellow-Green Group 149D. Inner Side: Yellow-Green Group 149D.

*After opening, petals.*—Outermost petals: Outer Side: Red Group 47D. Inner Side: Red Group 40A. Innermost petals: Outer Side: Red Group 50B. Inner Side: Red Group 40A.

*After opening, basal petal spots.*—Basal petal spot, outermost petals: Outer Side: Yellow-Green Group 150D. Inner Side: Yellow-Green Group 149D with intonations of Yellow-Green Group 154D. Basal petal spot, innermost petals: Outer Side: Yellow-Green 150D. Inner Side: Yellow-Green 149D. Variegations: None.

General tonality: On open flower, Orange-Red Group N30A. No change in the general tonality at the end of the 5$^{th}$ day. Afterwards, general tonality is Red Group 40A.

Petals:

*Petal count.*—Approximately 40–45 petals under normal conditions.

*Petal reflex.*—Petals reflex strongly.

*Petal edge.*—With a small point in the center and some marginal undulation of apex margin.

*Petal shape.*—Deltoid. Apex shape is pointed. Shape of base is rounded.

*Petal size.*—30–35 mm long; 25–30 mm wide.

*Thickness.*—Average.

*Petal arrangement.*—Generally in a regular pattern with overlapping edges.

Petaloids: Present.

*Petaloid count.*—Average of 3–5 per flower.

*Petaloid edge.*—Smooth. Color of margin, both inner and outer sides, Green-White Group 157C.

*Petaloid shape.*—With point in center of margin. Shape is linear to elliptic.

*Petaloid texture.*—Smooth.

*Petaloid size.*—Petaloids are 10–15 mm long and 5–7 mm wide.

*Petaloid color.*—Color of inner side is Orange-Red Group N30A. Color of outer side is Red Group 50A.

Reproductive organs:

*Pistils.*—Approximately 30–35 present. Stigmas: Location: Slightly superior in position to anthers. Color: Green-Yellow Group 1B. Styles: Length: 7–10 mm long. Color: Green-Yellow Group 1D. Intonations of Greyed-Red 182B.

*Stamens.*—Approximately 40–50 on average and regularly arranged. Anthers: Size: 2.5–3 mm long. Color: Outer margins — Greyed-Orange Group 164B. Inner stripe — Greyed-Orange Group 164A. Pollen: Absent. Filaments: Color: Yellow Group 2A. Length: 8–10 mm.

THE PLANT

*Plant growth.*—Moderate vigor. Compact growth habit. When grown as a budded nursery plant the average plant height is 70–75 cm and the average plant width is 60–65 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 10–12 per 10 cm of stem. Size: Average length: 9–11 mm. Color: Immature prickles: Yellow-Green Group 144A. Mature prickles: Greyed-Red Group 178A. Senescing to Greyed-Yellow 160B. Shape: Concave. Anthocyanin: Present on base of prickles. Color Greyed-Red Group 178B.

*Leaves and leaflets.*—Normally 5–7 leaflets on normal leaves in middle of the stem. Leaf size: 100–110 mm (l)×80–90 mm (w). Quantity: Average. Texture: Upper side of leaflet: Semi-glossy, smooth, and leathery. Under side of leaflet: Matte, smooth, and leathery. Color, mature foliage: Upper Leaf Surface: Green Group 137A. Lower Leaf Surface: Yellow-Green Group 147B. Color, juvenile foliage: Upper Leaf Surface: Green Group 137A. Lower Leaf Surface: Yellow-Green Group 147B. Anthocyanin intonation: Present. Location: Intonations present on the upper and lower surfaces of juvenile leaves. Color: Upper surface — Greyed-Purple 187A and Grey-Purple Group 187B. Lower surface — Greyed-Purple 183C.

*Stipules.*—Size: 12–15 mm long. Average 6 mm between the tips of the stipule. Main body of stipule 5 mm in width. Shape: Elongated, winged. Stipule color: Margins: Yellow-Green Group 146A. Center: Yellow-Green Group 146D. Anthocyanin Greyed-Red Group 181B. Presence of stipitate glands: Present on margins. Margins: Serrated. With stipitate glands.

*Petiole.*—Length: 5–10 mm. Diameter: 1–1.5 mm. Petiole color: Yellow-Green Group 146B. Anthocyanin present on juvenile tissue. Color: Greyed-Purple 183C. Underneath: Sparse prickles underneath: Prickle size: 1–2 mm length. Stipitate glands: Limited number of stipitate glands on margins.

*Rachis.*—Length: 18–20 mm. Diameter: 1–1.5 mm. Color: Yellow-Green Group 146D. Anthocyanin present on juvenile tissue. Color: Greyed-Purple 183A. Margins: With stipitate glands. Prickles: Occasional. Stipitate glands: Limited numbers of stipitate glands on margins.

*Leaflets.*—Size: Average size of the terminal leaflet is 50–55 mm (l)×30–35 mm (w). Shape: Round. Base: Ovate. Apex: Acute. Margins: Serrated. Texture: Leathery.

Hips/seed formation: Observed. Size: 18–24 mm (l)×12–15 (w). Color: Yellow-Green Group 144A senescing to Orange-Red Group 31B with intonations of Orange Group 26A and Orange Group 26B.

Winter hardiness: To date, the variety has been grown successfully in Zone 5.

Disease resistance: Very good resistance to powdery mildew, rust, and Black spot disease under normal growing conditions.

I claim:

1. A new and distinct variety of rose plant characterized by the following combination of characteristics:

(a) forms attractive, long lasting orange-red flowers;

(b) exhibits compact growth habit;

(c) propagates well using traditional methods, and;

(d) exhibits very good resistance to disease under normal growing conditions, substantially as herein illustrated and described.

* * * * *

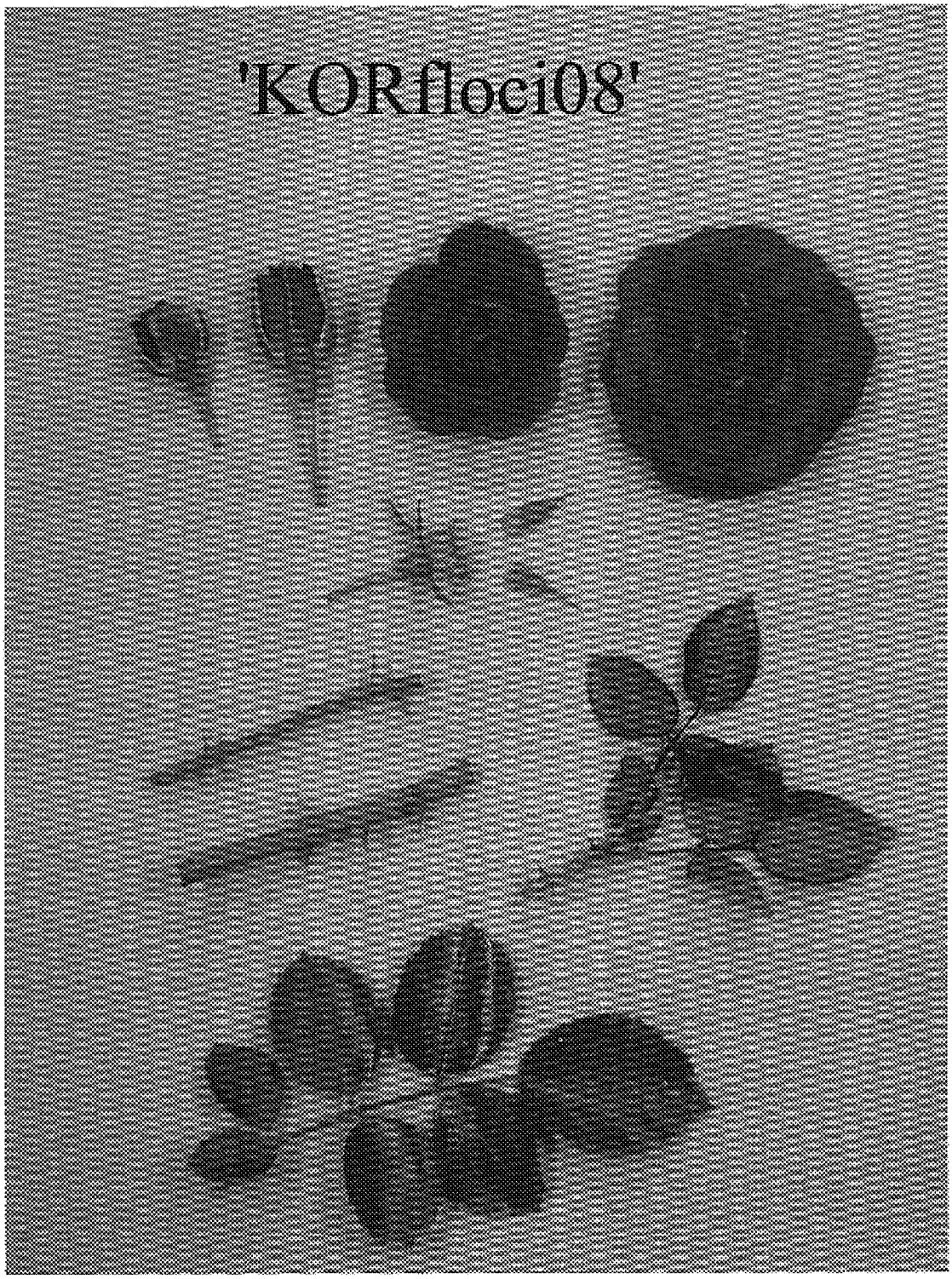
'KORfloci08'